(12) United States Patent
Abe

(10) Patent No.: US 6,585,722 B1
(45) Date of Patent: Jul. 1, 2003

(54) PHOTOCOAGULATION APPARATUS

(75) Inventor: Hitoshi Abe, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 166 days.

(21) Appl. No.: 09/630,363

(22) Filed: Aug. 1, 2000

(30) Foreign Application Priority Data

Aug. 5, 1999 (JP) .......................................... 11-221894

(51) Int. Cl.7 .............................................. A61B 18/18
(52) U.S. Cl. .............................. 606/4; 606/3; 606/10; 606/12; 606/13
(58) Field of Search ............................ 606/3, 4, 6, 10, 606/12, 13

(56) References Cited

U.S. PATENT DOCUMENTS

| | | | |
|---|---|---|---|
| 4,719,912 A | * 1/1988 | Weinberg et al. | ......... 128/303.1 |
| 4,741,612 A | 5/1988 | Birngruber et al. | |
| 4,758,081 A | 7/1988 | Barnes | |
| 4,880,001 A | 11/1989 | Weinberg | |
| 5,923,399 A | 7/1999 | Van de Velde | |
| 6,346,100 B1 | * 2/2002 | Tano et al. | ..................... 606/10 |

FOREIGN PATENT DOCUMENTS

| | | |
|---|---|---|
| DE | 3607721 A | 9/1987 |
| DE | 19635998 C | 4/1998 |
| EP | 0363221 A | 4/1990 |
| EP | 0697611 A | 2/1996 |
| GB | 2317227 A | 3/1998 |
| JP | 60-500603 | 5/1985 |
| JP | 5-337089 | 12/1993 |
| JP | 6-254112 | 9/1994 |

* cited by examiner

Primary Examiner—Teresa Walberg
Assistant Examiner—Shawntina Fuqua
(74) Attorney, Agent, or Firm—Oliff & Berridge, PLC

(57) ABSTRACT

A photocoagulation apparatus for coagulating an affected part of a patient by irradiating the part with a treatment laser beam emitted from a laser oscillator (10) is disclosed. The apparatus includes an input section (3) for setting an irradiation condition of the treatment laser beam, a detecting section (27, 40–43, 46, 47, 51) for optically detecting a coagulating state of a coagulation part produced by irradiation of the treatment beam, an analysis section (51) for analyzing the coagulating state detected by the detection section as compared with a desired coagulating state to be produced by irradiation of the treatment laser beam under the irradiation condition set with the input section, and a control section (50) for instructing a change in the irradiation condition as needed based on a result of analysis by the analysis section.

13 Claims, 6 Drawing Sheets

• COAGULATION SPOT

PHOTOCOAGULATION APPARATUS

BACKGROUND OF THE INVENTION

1. Field of the Invention

The present invention relates to a photocoagulation apparatus for photocoagulating an affected part (a treatment part) by irradiating the part with a treatment laser beam.

2. Description of Related Art

Conventionally, there has been known a photocoagulation apparatus for photocoagulating an affected part of a patient by irradiating the part with a treatment laser beam while allowing an operator to observe the affected part through an observation optical system such as a slit-lamp and others. In particular, an ophthalmic photocoagulation apparatus is arranged to utilize the thermal effect of laser to produce protein coagulation in the tissue of the fundus of a patient's eye. This apparatus is used for treatment for a macular functional disorder and a visual functional high disorder. A white spot which is generated from the protein coagulation is called a coagulation spot. The operator would empirically adjust laser irradiation conditions such as power, time, etc. of the treatment laser beam to be irradiated, while observing a forming state (progress) of the coagulation spot.

On the other hand, in an operation for quasi panretinal photocoagulation (quasi-PRP), for example, plural coagulation pots each having a substantial uniform diameter of 500–600 μm have to be produced over the affected part. FIG. 7 shows a schematic image of an eye fundus with a number of coagulation spots produced.

In this case, it is necessary that the coagulation spots are produced at various sites in the affected part as shown in FIG. 7. However, coagulating conditions and states depend on the light-absorbing property of the tissue at each site in the affected part. Even if the operator adjusts the irradiation conditions (power, time, etc. of laser irradiation) of the treatment laser beam, a coagulation spot could not always be formed as intended in each irradiation site.

SUMMARY OF THE INVENTION

The present invention has been made in view of the above circumstances and has an object to overcome the above problems and to provide a photocoagulation apparatus which is simply operable by an operator to produce coagulation spots each being uniform in color and spot size in an affected part irrespective of light-absorbing property of the tissue of the affected part.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a photocoagulation apparatus for coagulating an affected part of a patient by irradiating the part with a treatment laser beam emitted from a laser oscillator, including: input means for setting an irradiation condition of the treatment laser beam; detection means for optically detecting a coagulating state of a coagulation part produced by irradiation of the treatment laser beam; analysis means for analyzing the coagulating state detected by the detection means as compared with a desired coagulating state to be produced by irradiation of the treatment laser beam under the irradiation condition set with the input means; and control means for instructing a change in the irradiation condition as needed based on a result of analysis by the analysis means.

According to another aspect of the present invention, there is provided a photocoagulation apparatus for coagulating an affected part of a patient by irradiating the part with a treatment laser beam, the apparatus including: an input section provided with keys for setting an irradiation condition including at least either irradiation power or irradiation time of the treatment laser beam; an irradiation optical system including a laser oscillator which emits the treatment laser beam, for delivering the treatment laser beam emitted from the laser oscillator to the affected part to irradiate the part; a photographing optical system including a photoelectric image pick-up device for photographing an area including the affected part; video image processing means for processing an image of the area photographed by the photographing optical system to take image data of a coagulation spot produced by irradiation of the treatment laser beam from the image data of the photographed area, the video image processing means being connected with the photoelectric image pick-up device; analysis means for analyzing a forming state of the coagulation spot of which the image data is taken by the video image processing means as compared with a desired forming state of a coagulation spot to be produced by irradiation of the treatment laser beam under the irradiation condition set with the input section, the analysis means being connected with the video image processing means; and control means for instructing a change in the irradiation condition as needed based on a result of analysis by the analysis means, the control means being connected with the analysis means.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
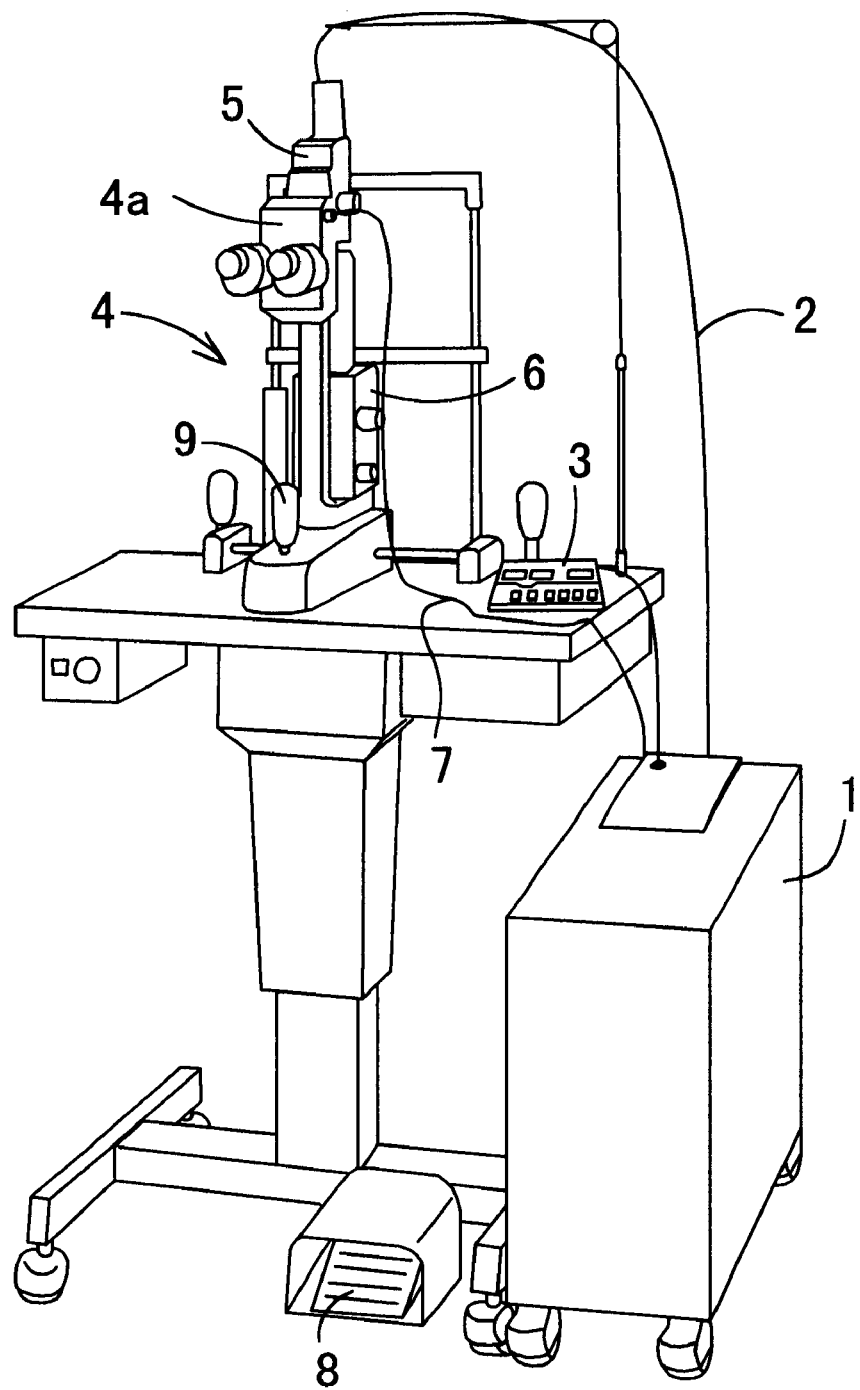
FIG. 1 is a perspective view of a photocoagulation apparatus in an embodiment according to the present invention.

A detailed description of a preferred embodiment of a photocoagulation apparatus embodying the present invention will now be given referring to the accompanying drawings. FIG. 1 is a perspective view of the photocoagulation apparatus, which is used for ophthalmic operations in the present embodiment. It is to be noted that irradiation of a treatment laser beam is hereinafter referred to as a laser irradiation.

Numeral 1 is a main unit which accommodates a laser source (a laser oscillator) 10 mentioned later, a laser delivery optical system, and others. Numeral 3 is a control unit used for setting necessary laser irradiation conditions such as laser irradiation power, laser irradiation time, etc. Numeral 4 is a slit-lamp delivery for irradiating a treatment laser beam (which is hereinafter simply referred to as a treatment beam) to an affected part of a patient's eye E, while allowing an operator to observe the eye E. The slit-lamp delivery 4 is constructed of a laser irradiation unit 5 for irradiating the treatment beam delivered therein from the laser source 10 through an optical fiber 2 to the eye E, an illumination unit 6 for slit-illuminating the patient's eye E, and a binocular microscope 4a. Numeral 7 is a cable used for transmitting video signals from a CCD camera (a photoelectric image pick-up device) 47 installed in the microscope 4a to a video image processing section 51 provided in the main unit 1. Numeral 8 is a footswitch used for generating a trigger signal to start laser irradiation.

Figure 2:
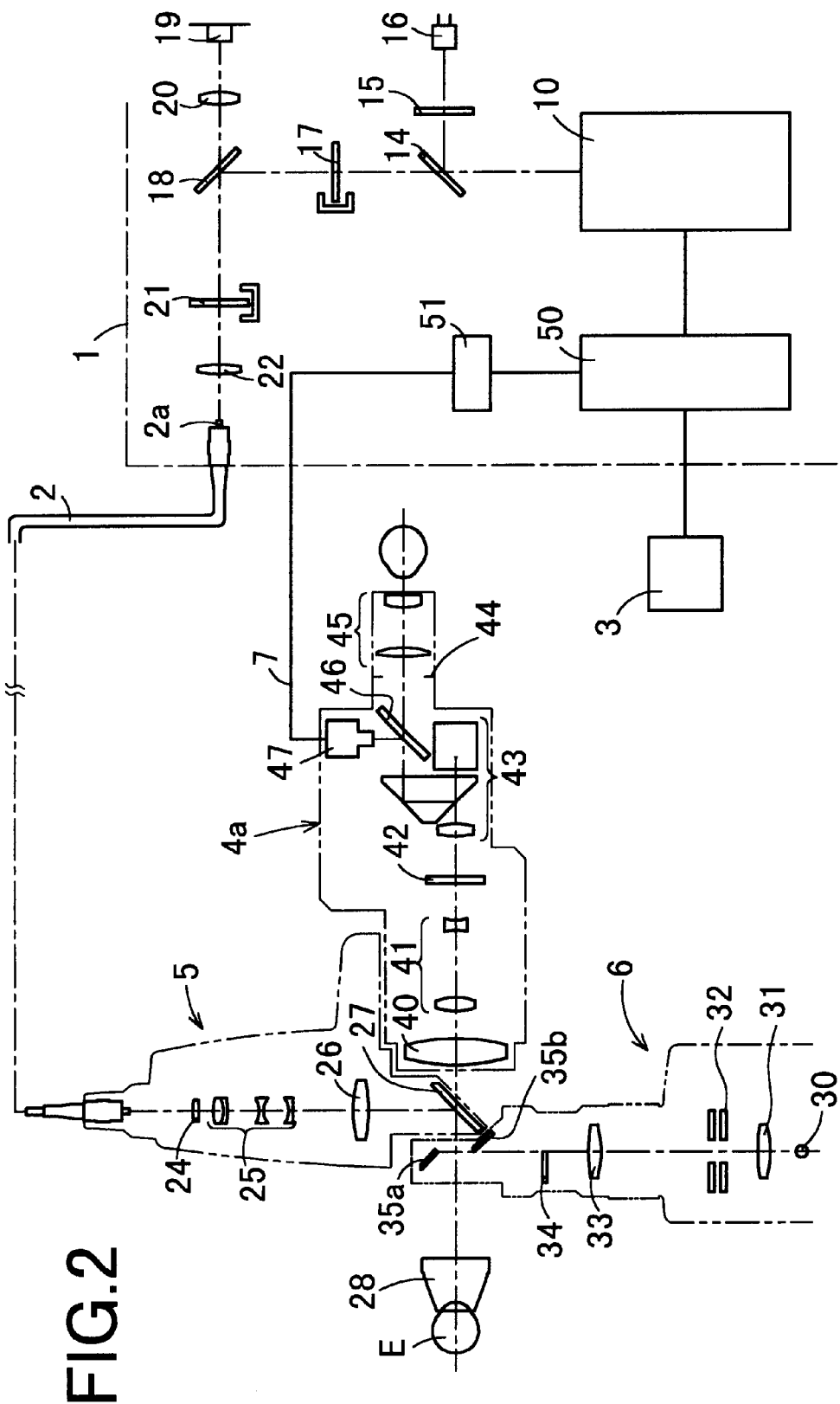
FIG. 2 is a schematic view of a structure of an optical system and a control system of the apparatus in the embodiment.

FIG. 2 is a schematic structural view of an optical system and a control system of the photocoagulation apparatus in the present embodiment. Numeral 10 is a laser source which emits a treatment beam. As this laser source 10 in the present embodiment, an Nd:YAG laser capable of oscillating a fundamental wavelength of 1064 nm is used to generate a green light of 532 nm (linearly polarized light) which is double the fundamental wavelength. Numeral 14 is a beam splitter for transmitting the major part of the treatment beam from the laser source 10 and reflecting a part of the treatment beam. The part of the treatment beam reflected by the beam splitter 14 passes through a diffusion plate 15 into a power sensor 16. Thus, the power sensor 16 can detect the power of the treatment beam emitted from the laser source 10.

Numeral 17 is a first safety shutter, which is inserted on the optical path of the treatment beam in order to intercept the beam in cases for example of occurrence of an abnormal event. Numeral 18 is a dichroic mirror. Numeral 19 is a laser source which emits an aiming light. As this laser source 19 in the present embodiment, a semiconductor laser which emits a red light is used. An aiming laser beam (which is simply hereinafter referred to as an aiming beam) emitted from the laser source 19 passes through a collimator lens 20 and then the collimated aiming beam is made coaxial with the treatment beam reflected by the dichroic mirror 18. Numeral 21 is a second safety shutter, which is put on the optical path during non-emission of the aiming beam. After passing by the shutter 21 positioned out of the optical path, the coaxial laser beams (the treatment beam and the aiming beam) are condensed by a condensing lens 22 to an entrance surface 2a of the fiber 2.

The laser beams delivered through the fiber 2 to the laser irradiation unit 5 is allowed to pass through a relay lens 24, zoom lenses 25, and an objective lens 26, and then is reflected by a movable mirror 27 toward a contact lens 28 put on the patient's eye E. The laser beams are thus irradiated to the affected part of the eye E. The zoom lenses 25 are movable in a direction of the optical axis for changing a spot size of the laser beams irradiated onto the affected part.

In the illumination unit 6, an illumination light emitted from an illumination source 30 passes through a condensing lens 31, a slit plate 32, a projection lens 33, and then is reflected by splitting mirrors 35a and 35b toward the eye E. The eye E is thus illuminated through the contact lens 28. The splitting mirrors 35a and 35b are adopted to split the illumination light so as not to intercept the optical path of the laser beams reflected by or passed through the movable mirror 27.

Numeral 34 is a correcting lens for correcting a length of the optical path of the illumination light to be reflected by the splitting mirror 35a.

The binocular microscope 4a is internally provided with an objective lens 40, variable magnification lenses 41, a protective filter 42, a group of erect prisms 43, a field diaphragm 44, and eyepieces 45. These components are arranged in pairs for binocular observation, only one of which is illustrated in FIG. 2. A half mirror 46 is also disposed on an observing optical path between the erect prism 43 and the field diaphragm 44 in either one of the paired components. The light reflected by the half mirror 46 will be received by the CCD camera 47.

Numeral 51 is a video image processing section including a memory for recording a forming state (progress) of the coagulation spot photographed by the camera 47. In the present embodiment, this camera 47 photographs the area of the eye fundus including the affected part, and the image processing section 51 takes (extracts) the image data of the coagulation spot from the image data of the photographed area of the eye fundus for the purpose of comparison and analysis of coagulation spots. The section 51 makes a comparison and analysis between the recorded forming state of the coagulation spot and a forming state of a coagulation spot produced by subsequent laser irradiation. The section 51 then transmits the analytical data to a control section 50. This control section 50 controls the laser source 10 based on the laser irradiation conditions set on the control unit 3 and the analytical data on the forming state of the coagulation spot transmitted from the video image processing section 51.

Figure 3:
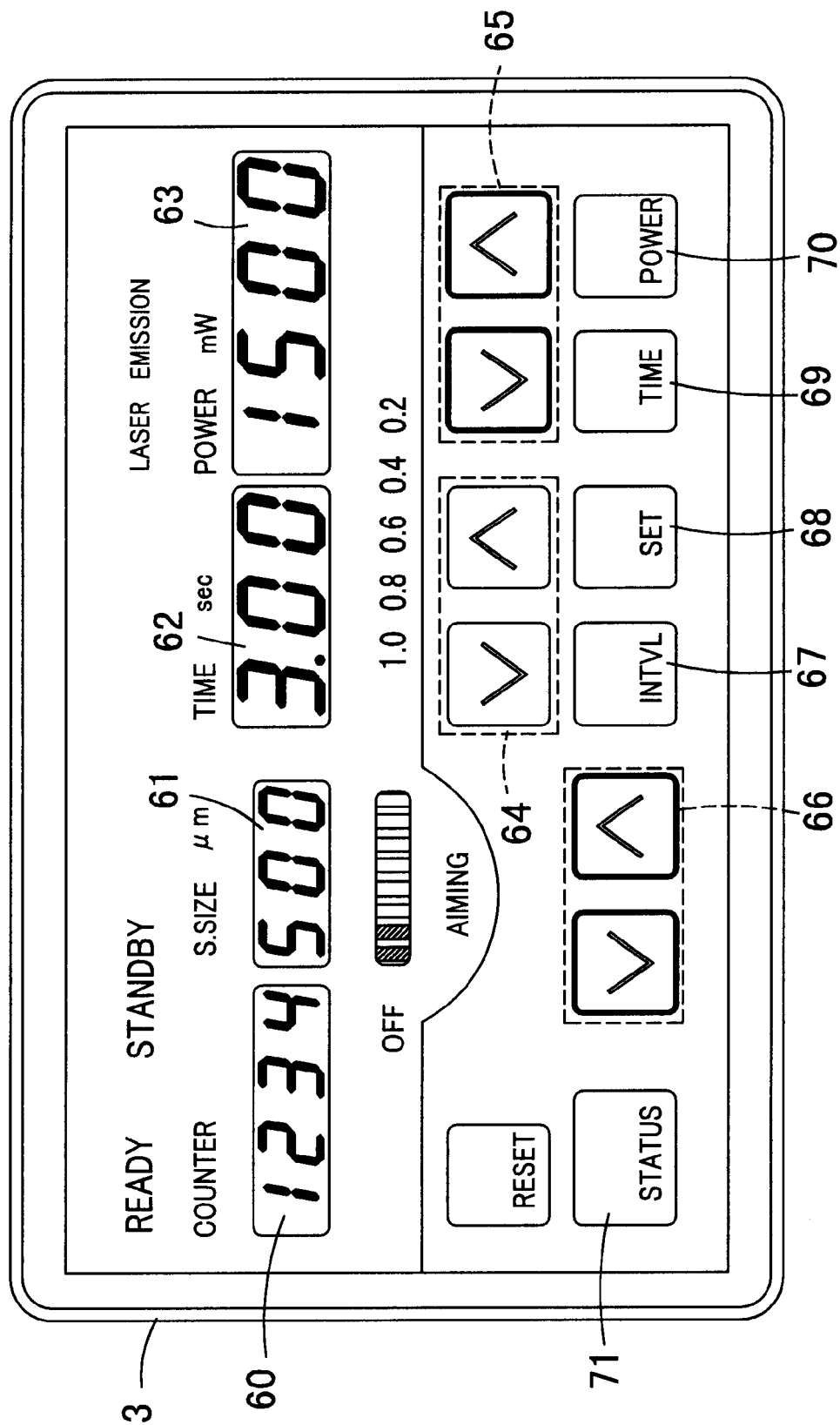
FIG. 3 is a plane view of a control unit in the embodiment.

FIG. 3 is a plane view of the control unit 3. Numeral 60 is a counter display part which displays the total number of emissions of the treatment beam. Numeral 61 is a spot diameter display part which displays the spot diameter (spot size) of the treatment beam to be irradiated to the affected part. This spot diameter is changeable in 10 $\mu$m step in the 50–500 $\mu$m range by operation of a change knob not illustrated. Numeral 62 is a time display part which displays the time duration of laser irradiation which is set by operation of time setting keys 64. That is to say, upon press of the footswitch 8 to generate a trigger signal, causing the start of laser irradiation, the laser irradiation is performed only for the time set with the time setting keys 64.

Numeral 63 is a power display part which displays the power of the treatment beam to be irradiated, which is set with power setting keys 65. Numeral 66 is an aiming control key used for adjustment of the luminous intensity of the aiming beam. Numeral 67 is an INTERVAL switch used for setting a time interval between emissions of the treatment beam irradiated continually. The time interval can be changed in 0.2 sec. step in a range of 0.2 to 1.0 sec.

Numeral 68 is a SET switch used for storing a forming state of a coagulation spot produced in the fundus of the eye E by laser irradiation, in the video image processing section 51. With use of the SET switch 68, the control section 50 can control the laser irradiation power, the laser irradiation time, etc. so as to produce a coagulation spot with substantially the same forming state as that of the coagulation spot recorded in the video image processing section 51. The detail thereof will be mentioned later. In a case of the laser irradiation control using the SET switch 68, if the laser irradiation is desired to be controlled based on only the irradiation power of laser without change of an irradiation time, a TIME switch 69 is used. Alternatively, if the laser irradiation is desired to be controlled based on only the irradiation time without change of the irradiation power, a POWER switch 70 is used. Numeral 71 is a STATUS switch used for switching between a laser irradiation enabled status and a laser irradiation disabled status.

Next, operations of the photocoagulation apparatus constructed as above will be explained below. At first, operations of recording the forming states of coagulation spots in the video image processing section 51 with the use of the SET switch 68.

The operator first observes the fundus of the eye E through the microscope 4a, the eye E being illuminated by the illumination light emitted from the illumination unit 6, and operates the aiming control keys 66 to turn on the aiming light source 19. Upon setting irradiation of the aiming beam, the control section 50 causes the shutter 21 to move out of the optical path.

The operator, observing the aiming beam irradiated to the eye fundus, operates a joystick 9 arranged on the operator's side (see FIG. 1) or an unillustrated manipulator to make alignment of the apparatus with respect to the affected part of the eye E. Subsequently, the laser irradiation conditions are determined; the operator sets a spot diameter of the treatment beam with an unillustrated change knob and sets irradiation time, irradiation power, time interval, etc. with the corresponding switches or keys on the control unit 3. The set conditions are determined according to the conditions of the affected part based on the operator's experiences.

After determination of the laser irradiation conditions, the operator adjusts the aiming beam to the irradiation site (the affected part) and presses the footswitch 8 to generate a trigger signal to start the laser irradiation, the trigger signal being transmitted to the control section 50. The control section 50 controls the laser source 10 to emit the treatment beam based on the set laser irradiation conditions to irradiate the fundus of the eye E, thus producing a coagulation spot therein. After that, the operator stops pressing the footswitch 8 to temporarily stop the laser irradiation for confirmation of the forming state of the coagulation spot. After stop of the laser irradiation, the operator should observe the forming state of the coagulation spot, and reconsider and change the laser irradiation conditions if needed.

When the coagulation spot with a good forming state and an appropriate color and spot size for the treatment intended this time can be produced, a proper (desired) forming state is recorded with reference to this forming state of the coagulation spot produced as above.

To be more specific, in order to record the desired forming state of a coagulation spot, the operator presses the SET switch 68 and then operates the apparatus to perform laser irradiation, under the same laser irradiation conditions as in the above last irradiation, with respect to a site (an affected part) which has almost the same light-absorbing property as the previously irradiated site. Upon press of the SET switch 68, the video image processing section 51 starts to record the image data transmitted from the camera 47. When the coagulation spot with a forming state almost identical to that in the last laser irradiation is produced, the operator stops the laser irradiation and presses the SET switch 68 again, causing the image processing section 51 to stop recording the image data. The image processing section 51 checks variations with time in color and spot size of the coagulation spot from the laser irradiation start in infinitesimal time intervals, and records those variations as a desired forming state of a coagulation spot. The color of the coagulation spot is generally white. The image processing section 51 thus uses the degree of shade of white as a factor to compare the colors between the coagulation spots.

Figure 4:
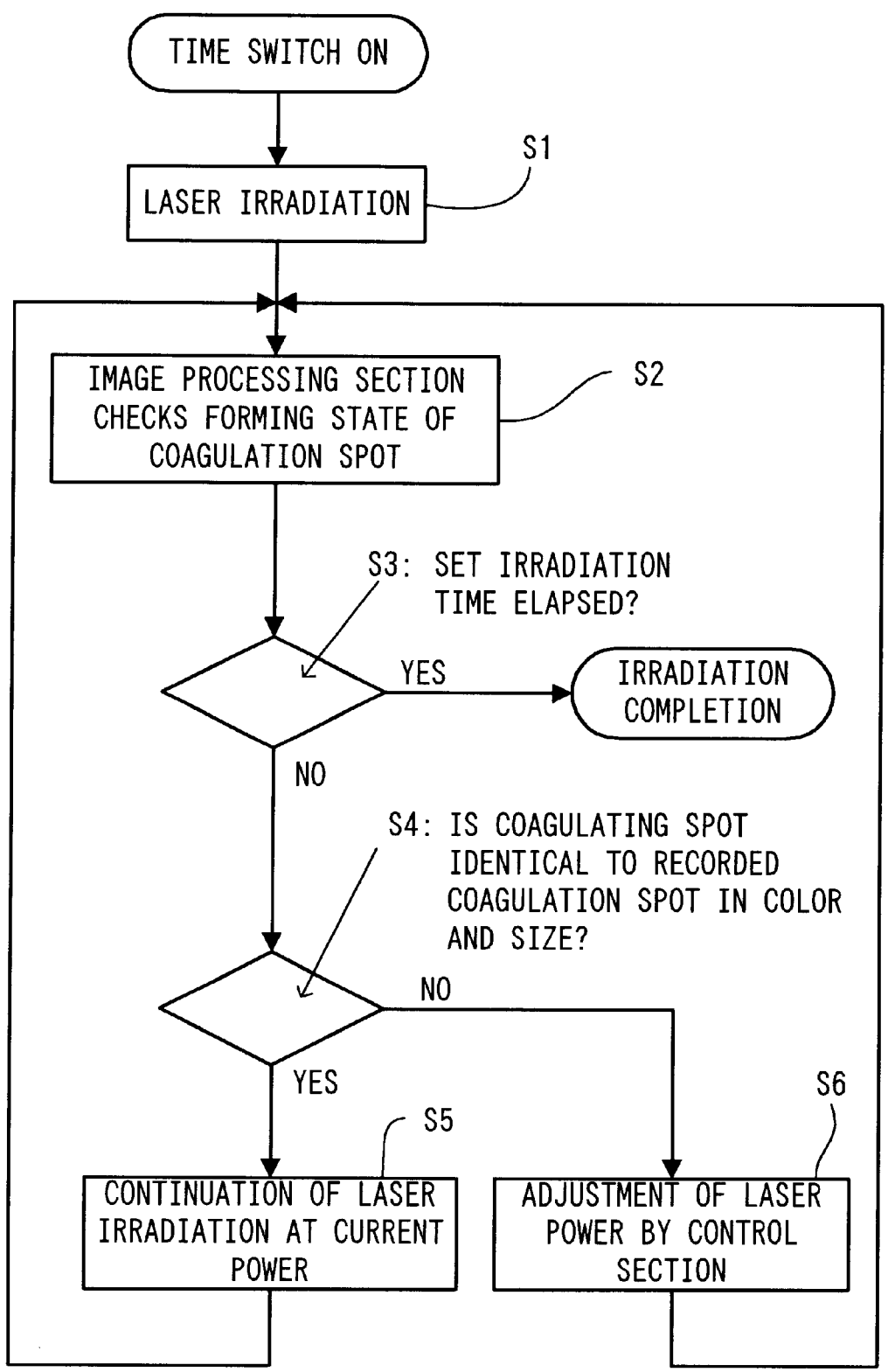
FIG. 4 is a flowchart of operations for laser irradiation with a TIME switch set in the embodiment.
Figure 5:
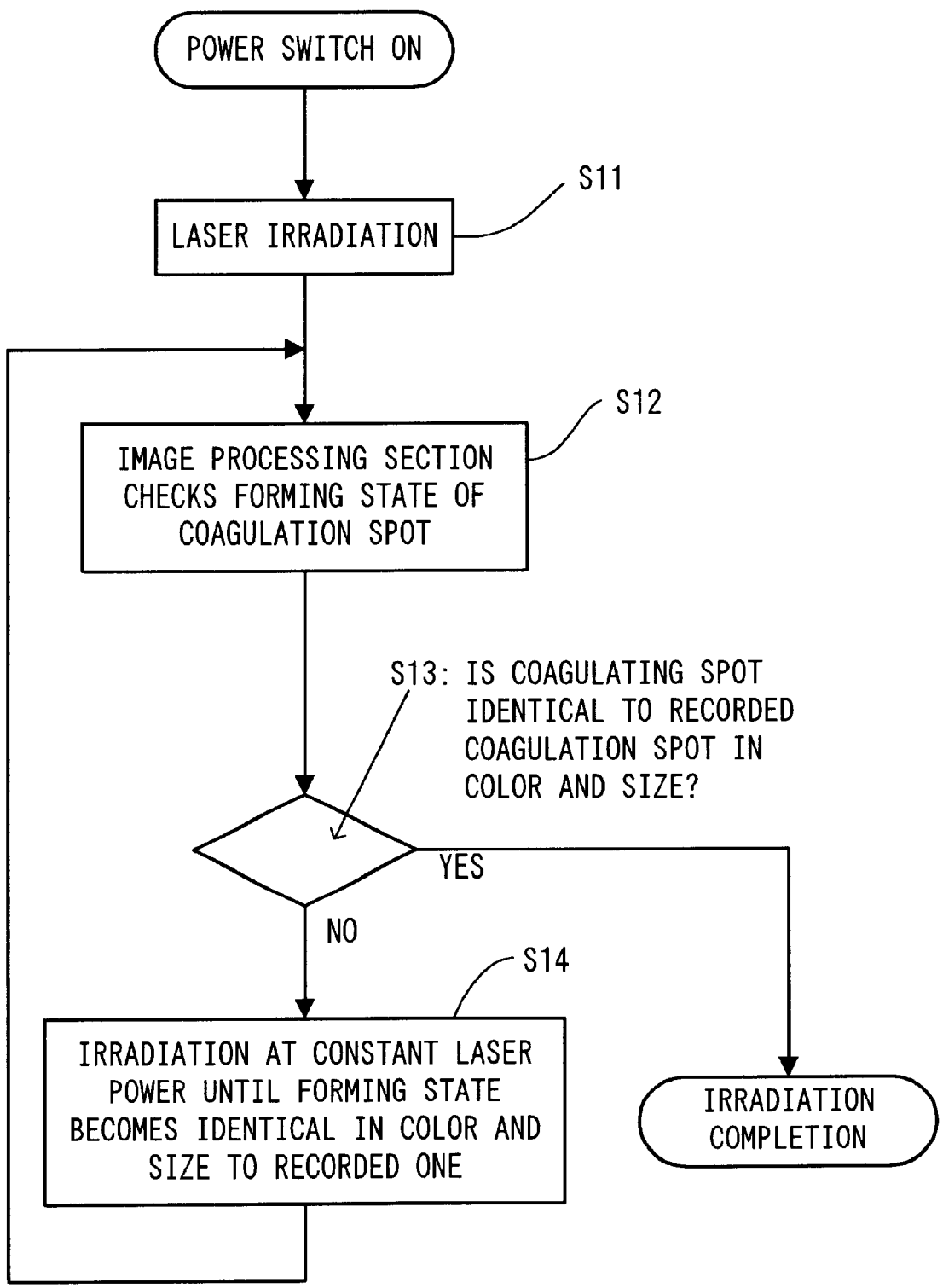
FIG. 5 is a flowchart of operations for laser irradiation with a POWER switch set in the embodiment.
Figure 6:
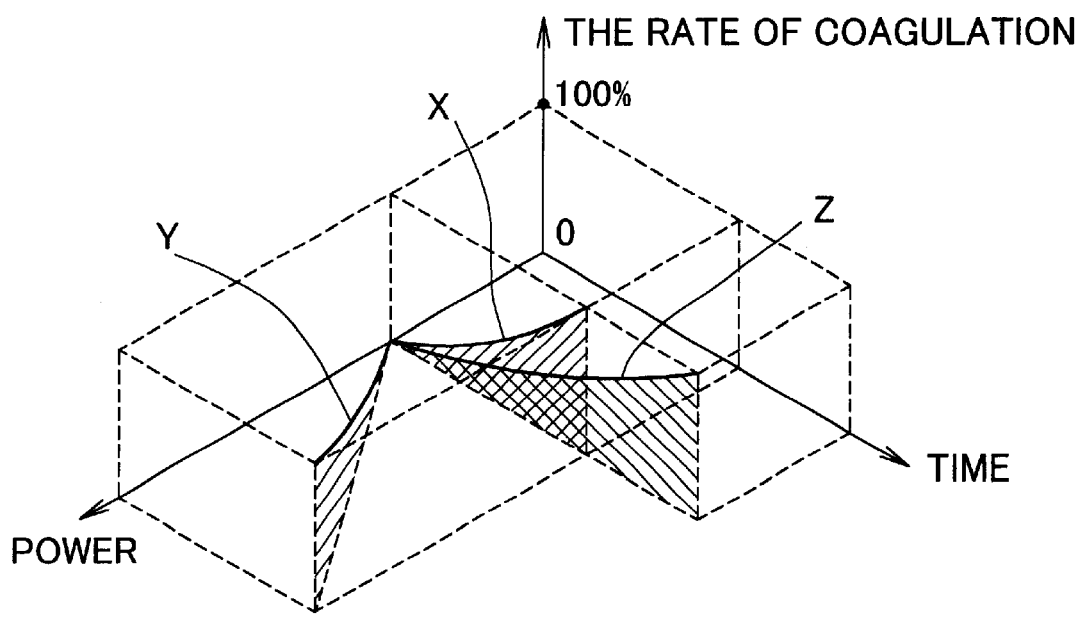
FIG. 6 is a graph of showing a relationship between forming states of coagulation spots in relation to irradiation time and irradiation power.

Next, explanation is made on the control of subsequent laser irradiation to the above to produce a coagulation spot with the same forming state as the recorded forming state, referring to FIGS. 4 to 6. FIG. 4 is a flowchart of the laser irradiation control executed with the TIME switch 69 set. FIG. 5 is a flowchart of the laser irradiation performed with the POWER switch 70 set. FIG. 6 is a graph of showing a relationship between forming states (the rate of coagulation) of coagulation spots in relation to irradiation time and irradiation power. In FIG. 6, a curve X shows a proper forming state of a coagulation spot which has been recorded in the memory of the video image processing section 51, a curve Y shows a forming state of a coagulation spot produced by the laser irradiation at the adjusted power and the same irradiation time as that for the coagulation spot X, and a curve Z shows a forming state of a coagulation spot produced by the laser irradiation at the adjusted irradiation time and the same irradiation power as that for the coagulation spot X.

The case of using the TIME switch 69 is first explained.

After the record of the desired forming state of the coagulation spot with use of the SET switch 68 as described above, the operator presses the TIME switch 69 and then the footswitch 8 to start the laser irradiation (S1). Upon start of the laser irradiation, the image processing section 51 compares, in infinitesimal time intervals, the variations with time in color and spot size of the coagulation spot being produced in the fundus of the eye E with those of the coagulation spot previously produced and recorded as above (S2). This comparison is started from the irradiation start time. The positions of the coagulation spots to be compared may be identified by detecting the sites of which image states vary with time in the images of the area photographed by the camera 47.

The image processing section 51 continuously transmits analytical data on differences in color and spot size between the coagulation spots in infinitesimal time intervals. The control section 50 controls the laser irradiation based on the analytical data transmitted from the image processing section 51 so that the forming state of the current coagulation spot corresponds all the time to the desired forming state of the coagulation spot recorded in advance. Namely, when the coagulation spot is identical in color and spot size to the recorded one (S4: YES), the control section 50 controls the laser source 10 to continuously emit the treatment beam at current power (S5). Alternatively, when NO in S4, the control section 50 adjusts the power of the treatment beam to be emitted from the laser source 10 (S6). The irradiation power may be adjusted by an increment or decrement of a predetermined value. Alternatively, the color and the spot size of the coagulation spot in relation to the irradiation power may be quantitatively determined in advance according to various sites in an affected part. Based on those data, an adjusting value of the irradiation power is determined by an algorithm. The control section 50 continuously controls the laser source 10 until the irradiation time set in advance has elapsed. When the predetermined time elapsed (S3: YES), the irradiation is completed.

In the above manner, when the TIME switch 69 is pressed to fix the irradiation time, the laser irradiation can be completed within the irradiation time set in advance. This can provide an advantage of preventing the occurrence of timing lags (differences) between dozens or hundreds of emissions of the treatment beam for production of many coagulation spots over the affected part.

Figure 7:
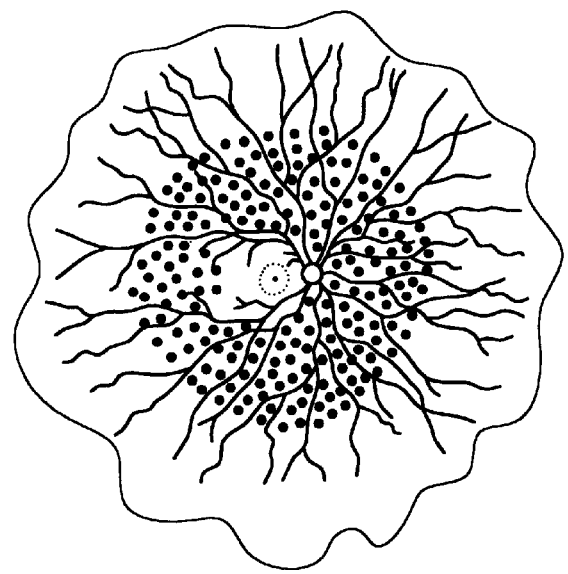
FIG. 7 is a schematic view of showing an eye fundus image with many sites operated by quasi panretinal photocoagulation (quasi-PRP) operation.

In general, operators tend to perform coagulating operations in individual rhythms or timings to produce many coagulation spots as shown in FIG. 7. According to site in which a coagulation spot is produced, there may be a case where a coagulation spot having a predetermined color and spot size could not be produced within the set time. In such the case, the progress of the coagulating state (color and spot size) is measured, and the power of the laser is controlled to increase sufficiently to produce a coagulation spot having a predetermined color and spot size.

Next, the case of using the POWER switch 70 is explained below, referring to FIG. 5. After the record of the desired forming state of the coagulation spot by use of the SET switch 68, the operator presses the POWER switch 70 and then the footswitch 8 to start the laser irradiation (S11). Upon start of the laser irradiation, the image processing section 51 compares, in infinitesimal time intervals, the variations with time in color and spot size of the coagulation spot in process of being produced in the fundus of the eye E with those of the coagulation spot recorded in advance (S12).

The image processing section 51 continuously transmits analytical data on the coagulation spots compared in infinitesimal time intervals to the control section 50. Based on the analytical data transmitted from the image processing section 51, the control section 50 checks whether the coagulation spot in process of being produced (namely, the current coagulation spot) is identical in color and spot size to the recorded coagulation spot (S13). If NO in S13, the control section 50 operates to continue the laser irradiation at constant power (S14). Then, the control section 50 stops the laser irradiation from the laser source 10 at the time when the forming state of the current coagulation spot becomes identical to the desired forming state of the previous coagulation spot (finally obtained at completion of the irradiation time of the treatment beam) recorded in advance (S13: YES).

When the POWER switch 70 is pressed as above, maintaining the treatment beam to be irradiated at constant power, the laser source 10 is not needed continuously adjusting and a load on the apparatus can be reduced.

The control of the laser irradiation power and the control of the laser irradiation time are of different advantages respectively. The operator may choose an appropriate one of the controls as needed. In both the controls, the laser irradiation conditions are adjusted so as to produce a coagulation spot with a forming state identical to the desired forming state of the coagulation spot produced and recorded in advance. Accordingly, even if sites having different light-absorbing properties to the treatment beam are irradiated, the coagulation spots can be produced with a uniform forming state without the need of changing the laser irradiation conditions every time.

The controls of the laser irradiation power and the laser irradiation time are preferably needed to have some upper limitations in irradiation power and irradiation time to prevent the application of loads on the patient.

The present invention may be embodied in other specific forms without departing from the spirit or essential characteristics thereof.

In the above embodiment, the laser irradiation control is performed during irradiation of the treatment beam based on the image data of the photographed eye fundus according to variations with time of the coagulation spot. For example, an alternative manner may be adopted; the laser irradiation is carried out without changing irradiation power and time during laser irradiation, and then the forming state of the coagulation spot is compared with the desired forming state of the coagulation spot recorded in advance to adjust laser irradiation conditions as needed for the subsequent laser irradiation.

In the above embodiment, either the irradiation power or the irradiation time is used as a factor of the laser irradiation control. Both the irradiation power and the irradiation time may be controlled at the same time.

In the above embodiment, the image processing section 51 takes (extracts) the coagulation spot portion from the image data of the photographed eye fundus to perform record, comparison and analysis of the forming state of the coagulation spot. An alternative manner is to cause the image analyzing section (image processing section) to take (extract) only the coagulation spot portion from the image data of the eye fundus photographed by the CCD camera and the control section to make record and analysis thereof.

As described above, the photocoagulation apparatus in the above embodiment according to the present invention is arranged capable of recognizing the forming state of the coagulation spot by laser irradiation and adjusting the laser irradiation conditions based on the recognized results. Thus, substantially uniform coagulation spots can be produced irrespective of the light-absorbing properties of tissue of the affected part according to sites therein, enabling a reduction in load on the operator.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A photocoagulation apparatus for forming a coagulation spot in a part to be treated of a patient by irradiating the part with a treatment laser beam emitted from a laser oscillator, comprising:

input means for setting at least one of laser irradiation output and laser irradiation time as a treatment parameter;

detection means having an image pick-up device, for optically detecting the coagulation spot formed by irradiation of the treatment laser beam;

memory means for storing image data of the coagulation spot in association with a corresponding treatment parameter as a reference;

analysis means for comparing colors between image data of the coagulation spot newly detected by the detection means and the image data of the coagulation spot stored as the reference; and control means for changing the treatment parameter based on a result of comparison by the analysis means.

2. The photocoagulation apparatus according to claim 1, wherein the detection means includes:

a photographing optical system having the image pick-up device for photographing an area including the coagulation spot; and a video image processing section for processing an image of the area photographed by the photographing optical system to take out the image data of the coagulation spot.

3. The photocoagulation apparatus according to claim 2, wherein the video image processing section includes processing means for taking out the image data of the coagulation spot from the images photographed before and after the irradiation of the treatment laser beam.

4. The photocoagulation apparatus according to claim 1, wherein the control means includes instruction means for transmitting an instruction signal to change the treatment parameter to a controller of the laser oscillator.

5. The photocoagulation apparatus according to claim 1, further including selection means for selecting the treatment parameter to be changed by the control means.

6. The photocoagulation apparatus according to claim 1, further including a fundus photocoagulation apparatus provided with a slit-lamp optical system.

7. A photocoagulation apparatus for forming a coagulation spot in a part to be treated of a patient by irradiating the part with a treatment laser beam, the apparatus comprising:

an input section provided with keys for setting at least either irradiation power or irradiation time of the treatment laser beam as a treatment parameter;

an irradiation optical system including a laser oscillator which emits the treatment laser beam, for delivering the treatment laser beam emitted from the laser oscillator to the part to irradiate the part;

a photographing optical system including a photoelectric image pick-up device, for photographing an area including the coagulation spot formed by irradiation of the treatment laser beam;

a video image processing unit which processes an image of the area photographed by the photographing optical system to take out image data of the coagulation spot;

a memory which stores image data of the coagulation spot in association with a corresponding treatment parameter as a reference;

an analysis unit which compares colors between image data of the coagulation spot newly taken out by the video image processing unit and the image data of the coagulation spot stored as the reference; and a control unit which changes the treatment parameter based on a result of comparison by the analysis unit.

8. The photocoagulation apparatus according to claim 7, wherein the video image processing unit takes out the image data of the coagulation spot from the images photographed before and after the irradiation of the treatment laser beam.

9. The photocoagulation apparatus according to claim 7, wherein the control unit transmits an instruction signal to change the treatment parameter to a controller of the laser oscillator.

10. The photocoagulation apparatus according to claim 7, wherein the input section includes selection keys for selecting the treatment parameter to be changed by the control unit.

11. The photocoagulation apparatus according to claim 7, further including a fundus photocoagulation apparatus provided with a slit-lamp optical system.

12. The photocoagulation apparatus according to claim 1, wherein the detection means detects the coagulation spot with time in the course of formation thereof, the memory means stores the image data of the coagulation spot showing changes with time, the analysis means compares change with time in color between the image data of the coagulation spot newly detected and the image data of the coagulation spot stored as the reference, and the control means changes the treatment parameter during the irradiation of the treatment laser beam.

13. The photocoagulation apparatus according to claim 7, wherein the video image processing unit takes out the image data of the coagulation spot with time in the course of formation thereof, the memory stores the image data of the coagulation spot showing changes with time, the analysis unit compares change with time in color between the image data of the coagulation spot newly taken out and the image data of the coagulation spot stored as the reference, and the control unit changes the treatment parameter during the irradiation of the treatment laser beam.

* * * * *